US011378538B2

United States Patent
Lee et al.

(10) Patent No.: US 11,378,538 B2
(45) Date of Patent: Jul. 5, 2022

(54) WATER DETECTOR

(71) Applicant: Nortek Security & Control LLC, Carlsbad, CA (US)

(72) Inventors: Ming Chuan Lee, ShenZhen (CN); Xuefeng Ma, ShenZhen (CN); Jian Hua Liu, ShenZhen (CN); Jian Hong Yin, ShenZhen (CN)

(73) Assignee: Nortek Security & Control LLC, Carlsbad, CA (US)

( * ) Notice: Subject to any disclaimer, the term of this patent is extended or adjusted under 35 U.S.C. 154(b) by 0 days.

(21) Appl. No.: 16/073,259

(22) PCT Filed: Sep. 28, 2017

(86) PCT No.: PCT/CN2017/103937
§ 371 (c)(1),
(2) Date: Jul. 26, 2018

(87) PCT Pub. No.: WO2019/061141
PCT Pub. Date: Apr. 4, 2019

(65) Prior Publication Data
US 2020/0264120 A1 Aug. 20, 2020

(51) Int. Cl.
*G01N 27/22* (2006.01)
*G06F 9/4401* (2018.01)
(Continued)

(52) U.S. Cl.
CPC ............ *G01N 27/223* (2013.01); *G01M 3/04* (2013.01); *G06F 9/4418* (2013.01); *H04W 4/80* (2018.02)

(58) Field of Classification Search
CPC .... G01N 27/223; G01N 22/04; G01N 27/228; G01N 33/46; G01R 27/2605;
(Continued)

(56) References Cited

U.S. PATENT DOCUMENTS 4,135,151 A 1/1979 Rogers et al.
4,227,190 A 10/1980 Kelley
(Continued)

FOREIGN PATENT DOCUMENTS

CN 104240448 A 12/2014
CN 205579734 U 9/2016
(Continued)

OTHER PUBLICATIONS

"International Application Serial No. PCT/CN2017/103937, International Search Report dated Jun. 22, 2018", 5 pgs.
(Continued)

*Primary Examiner* — Douglas X Rodriguez
*Assistant Examiner* — Trung Q Nguyen
(74) *Attorney, Agent, or Firm* — Schwegman Lundberg & Woessner, P.A.

(57) ABSTRACT

A water detection device (100) may have a water sensor on both a top and bottom of the device. A water sensor circuit (1004,1006,1100, 1101) may be configured to detect water by delivering a signal may be delivered to an electrical contact (1104, 1132), and the presence of water may be determined based upon detection of the signal at the other contact (1106, 1134). The water sensor circuit device (1101) may be configured with a comparator (1116) that uses hysteresis to provide sensitivity to the presence or absence of water. In a battery-powered water sensor, the water detection signal may be delivered as an alternating signal using, e.g., a signal modulator circuit (e.g., an oscillator circuit (1114) and gate (1120) optionally coupled to a wake-sleep controller (1112)) that is coupled to a battery (133), which may avoid oxidation or other forms of ionic corrosion. In some examples, a water detection signal may be recurrently delivered to the first contact (1132) to conserve battery power.

10 Claims, 12 Drawing Sheets

(51) Int. Cl.
*H04W 4/80* (2018.01)
*G01M 3/04* (2006.01)

(58) Field of Classification Search
CPC ............ G01R 27/2611; G01R 27/2658; G01R 33/1223; G01F 23/222; G01F 23/26; G01M 3/04; G06F 9/4418; H04W 4/80
USPC .................. 324/750.01, 500, 507, 513, 523, 324/750.15–750.22, 754.19, 756.01, 324/762.01, 600, 612, 644, 76.11
See application file for complete search history.

(56) References Cited

U.S. PATENT DOCUMENTS

| | | | |
|---|---|---|---|
| 4,356,479 A | 10/1982 | Wilson | |
| 5,058,421 A | 10/1991 | Alexander et al. | |
| D360,153 S | 7/1995 | Chacchia | |
| 7,084,776 B2 | 8/2006 | Tacilauskas | |
| 9,582,987 B2 * | 2/2017 | Eskildsen | .............. G08C 17/02 |
| D802,462 S | 11/2017 | Morneau et al. | |
| D851,526 S | 6/2019 | Lee et al. | |
| 2007/0144253 A1 * | 6/2007 | Kobayashi | .............. G01F 23/28 |
| | | | 73/304 C |
| 2012/0312077 A1 | 12/2012 | Al-Harbi | |
| 2017/0258262 A1 * | 9/2017 | Atilla | ....................... A23F 5/267 |
| 2019/0027013 A1 * | 1/2019 | Sale | ........................ G08B 21/20 |

FOREIGN PATENT DOCUMENTS

| | | |
|---|---|---|
| CN | 206096127 U | 4/2017 |
| JP | 2001116648 A | 4/2001 |
| WO | WO-0192861 A2 | 12/2001 |
| WO | WO-2017115145 A1 | 7/2017 |
| WO | WO-2019061141 A1 | 4/2019 |

OTHER PUBLICATIONS

"International Application Serial No. PCT/CN2017/103937, Written Opinion dated Jun. 22, 2018", 4 pgs.

"U.S. Appl. No. 29/626,596, Notice of Allowance dated Jan. 28, 2019", 10 pgs.

* cited by examiner

WATER DETECTOR

CLAIM OF PRIORITY

This application is a U.S. National Stage Filing under 35 U.S.C. § 371 of International Patent Application No. PCT/CN2017,103937, filed on Sep. 28, 2017, the benefit of priority of which is claimed hereby, and which is incorporated by reference herein in its entirety.

TECHNICAL FIELD

This document relates generally to environmental sensors, and more particularly, but not by way of limitation, to systems, devices, and methods to detect the presence of liquid water.

BACKGROUND

The presence of unwanted liquid water may cause significant damage to property. For example, prolonged contact with water may damage items or structures made of wood or building materials such as sheetrock. Water may also cause corrosion of metallic surfaces, or shorting of electrical circuits. Water may also lead to the growth of mold. Early detection of water may allow for intervention to stop a water leak or otherwise prevent or avoid extended exposure to water.

SUMMARY

This document discusses, among other things, systems and methods to detect the presence of water.

An example (e.g., "Example 1") of subject matter (e.g., a water detection device or system) may include a housing, and a first water sensor coupled to the housing.

In Example 2, the subject matter of Example 1 may optionally be configured such that the first water sensor is at the top of the housing. The water detection device may further include a second water sensor at the bottom of the housing.

In Example 3, the subject matter of Example 1 may optionally be configured such that the housing has a concave top surface.

In Example 4, the subject matter of any one or more of Examples 1-3 may optionally be configured such the housing has a canal in the concave top surface configured to direct water toward the first water sensor.

In Example 5, the subject matter of any one or more of Examples 1-4 may optionally be configured such that the housing includes a removable cover. The water detection device may further include a circuit board, and a mechanically biased electrical contact coupled to the removable cover, the mechanically biased electrical contact electrically coupling the first water sensor to the circuit board.

In Example 6, the subject matter of any one or any combination of Examples 1-5 may optionally include a mechanically biased electrical contact in the form of a pogo pin.

In Example 7, the subject matter of any one or more of Examples 1-6 may optionally include one or more water detection circuits configured to process signals from the first water sensor and the second water sensor and declare a water event when water is detected at least one of the first water sensor or the second water sensor.

In Example 8, the subject matter of any one or more of Examples 1-7 may optionally include a wireless transceiver, wherein the water detection device is configured to send an alert signal via the wireless transceiver responsive to detection of water at least one of the first water sensor or the second water sensor.

In Example 9, the subject matter of any one or more of Examples 1-8 may optionally be configured such that the first water sensor includes a first electrical contact and a second electrical contact. The water detection device may further include a water detection circuit that is configured to deliver a water sensing pulse to the first electrical contact. The water sensing pulse may be detectable by the water detection circuit through the second electrical contact in the presence of water between the first electrical contact and second electrical contact.

In Example 10, the subject matter of any one or more of Examples 1-9 may optionally include a direct current power source. The water detection device may also include a signal modulator circuit that is coupled to the direct current power source and is configured to deliver the water sensing pulse as a pulse of alternating current to the first electrical contact.

In Example 11, the subject matter of any one or more of Examples 1-10 may optionally be configured to include a water detection circuit that is configured to recurrently or intermittently deliver the water sensing pulse at a sampling interval.

In Example 12, the subject matter of any one or more of Examples 1-11 may optionally be configured such that the water detection circuit includes, an oscillator circuit coupled to the first electrical contact and configured to deliver an oscillating pulse to the first electrical contact, an analog comparator circuit with hysteresis, the analog comparator circuit coupled to the second electrical contact, and a water alert circuit coupled to the analog comparator circuit. The water alert circuit configured to declare a water event alert responsive to detection of the oscillating pulse at the second electrical contact.

An example (e.g., "Example 13") of subject matter (e.g., a method) may include delivering an alternating current water sensing pulse to a first electrical contact, detecting the water sensing pulse as an attenuated signal at a second electrical contact, passing the attenuated signal through a low pass filter, applying the filtered signal as an input to a gate, applying an output of the gate as an input to a latch, and declaring a water event responsive to the input to the latch meeting a water event condition.

In Example 14, the subject matter of any one or any combination of Examples 1-13 may optionally be configured such that a water event condition includes a specified number of positive water signal sequential inputs.

In Example 15, the subject matter of any on or any combination of Examples 1-14 may include delivering the alternating current water sensing pulse according to a sampling interval.

An example (e.g., "Example 16") of subject matter (e.g., a water detection device or system) may include a housing, a first contact coupled to the housing, a second contact coupled to the housing, an oscillator circuit coupled to the first contact and configured to deliver an oscillating pulse to the first contact, an analog comparator circuit with hysteresis, the analog comparator circuit coupled to the second contact, and a water alert circuit coupled to the analog comparator circuit, the water alert circuit configured to declare a water event responsive to detection of the oscillating pulse at the second contact.

In Example 17, the subject matter of any one or any combination of Examples 1-16 may optionally be configured to include a water alert circuit includes a latch circuit configured to receive an input based upon a detected signal at the second contact and trigger a water alert when a water detection condition is satisfied.

In Example 18, the subject matter of any one or any combination of Examples 1-17 may optionally be configured to include a water alert circuit that includes a first gate coupled to the analog comparator circuit and a second gate coupled to the oscillator circuit. The output of the first gate and the output of the second gate being may be provided as inputs to the latch circuit.

In Example 19, the subject matter of any one or any combination of Examples 1-18 may optionally include a wake-sleep controller. The oscillating pulse may be intermittently delivered to the first contact based on a signal from the wake sleep controller.

In Example 20, the subject matter of any one or any combination of Examples 1-19 may optionally be configured to include an oscillator circuit generates a signal having a frequency between 6 and 50 kHz.

In Example 21, the subject matter of any one or any combination of Examples 1-20 may optionally an oscillator circuit that generates a signal having a frequency of about 25 kHz.

An example (e.g., "Example 22") of subject matter (e.g., a system or apparatus) may optionally combine any portion or combination of any portion of any one or more of Examples 1-35 to include "means for" performing any portion of any one or more of the functions or methods of Examples 1-35, or a "machine-readable medium" (e.g., massed, non-transitory, etc.) including instructions that, when performed by a machine, cause the machine to perform any portion of any one or more of the functions or methods of Examples 1-35.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
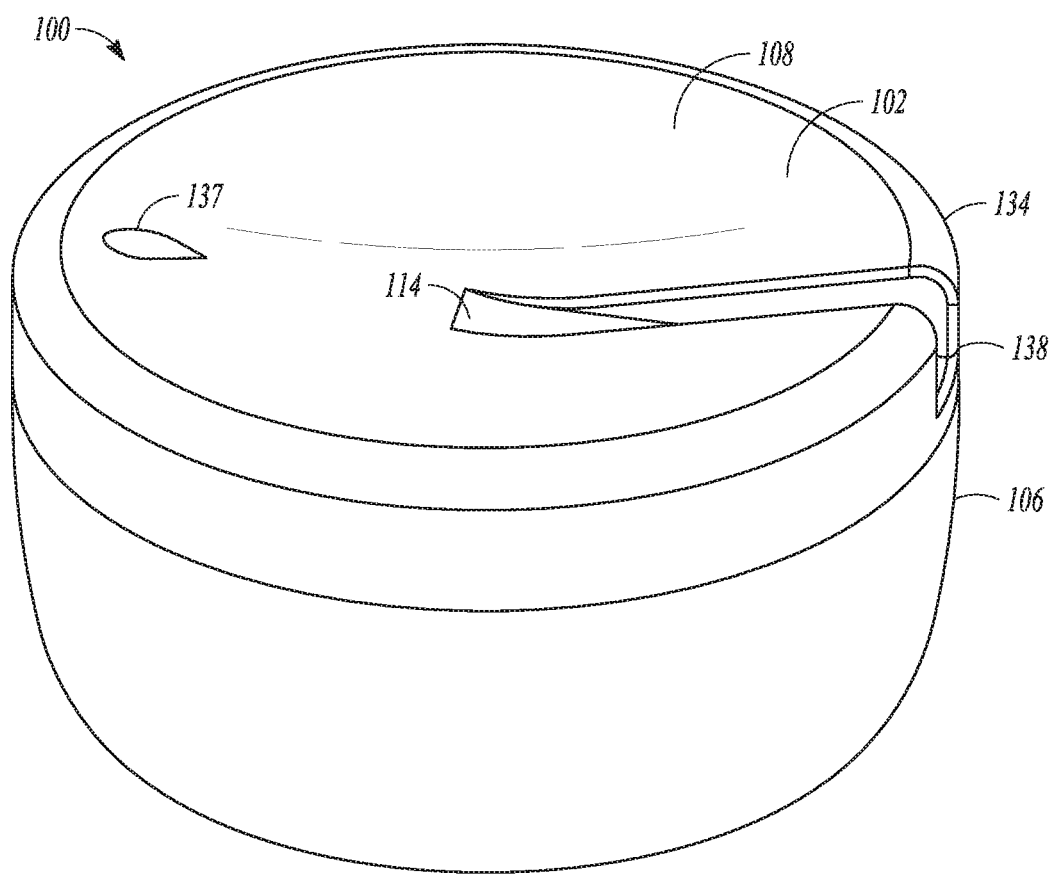
FIG. 1 is a perspective view illustration of an example water detection device.

The present inventors have recognized, among other things, that a water detection device may be constructed with water sensors on both a top side and a bottom side of a water detection device. A water detection device that has a water sensor on both a top and bottom of the device may be configured, for example, to detect water dripping onto the top side of the device (e.g., from a leaky sink or other plumbing component) as well as pooling water at the base of the device. The present inventors have further recognized that a water sensor circuit may be configured to detect water by delivering a signal may be delivered to an electrical contact, and the presence of water may be determined based upon detection of the signal at the other contact. The water sensor circuit device may be configured with a comparator that uses hysteresis to provide sensitivity to the presence or absence of water. In a battery-powered water sensor, the water detection signal may be delivered as an alternating signal using, e.g., a signal modulator circuit (e.g., an oscillator circuit and gate optionally coupled to a wake-sleep controller) that is coupled to a battery, which may avoid oxidation or other forms of ionic corrosion. In some examples, a water detection signal may be recurrently (e.g., intermittently) delivered to the first contact, which may save power.

An example water sensing device may include a housing, a cover, and one or more water detection circuits in the housing. The cover may include a concave top surface to collect water, and an optional channel to direct water toward electrical contacts on the top surface of the water sensing device. The water sensing device may also include mechanically-biased electrical contacts, such as pogo pins, that may electrically couple to the water detection circuit when a cover is assembled onto a housing portion of the water sensing device. The water detection circuit may include a signal modulator circuit that may be powered by a direct-current source (such as a battery). The water detection circuit may be configured to generate an alternating current water sensing pulse that may be delivered to one or more electrical contacts. The alternating current water sensing pulse may be delivered according to a sampling interval to conserve power. The use of an alternating current pulse may avoid corrosion at the electrical contacts. When water is present between the first electrical contact and the second electrical contact, the alternating current water sensing pulse generated by the signal modulator circuit may be detected via the second electrical contact and a water alert circuit coupled to the second electrical contact. A comparator circuit with hysteresis, coupled with a gate, may electrically connected to the second electrical contact and may be used to increase the sensitivity in detection of the attenuated water sensing pulse when the AC pulse conducts through accumulated water on top of or below. The received signal may be processed using a de-bouncing circuit (latch circuit), which may trigger a water alert when an alert condition is satisfied. In some examples, the example water detection device may include two water sensors: A top water sensor may be on a top surface of the water detection device, and may be configured, for example, to detect dripping water. A bottom water sensor may be on the bottom of the water detection device and may be configured, for example, to detect water that is pooling on a surface beneath the water sensor. The top water sensor and bottom water sensor may each include respective first and second electrical contacts that may be coupled to one or more water detection circuits that may trigger a water alert based upon electrical conduction across the first and second electrical contacts.

FIG. 1 is a perspective view illustration of an example water detection device 100.

Figure 2A:
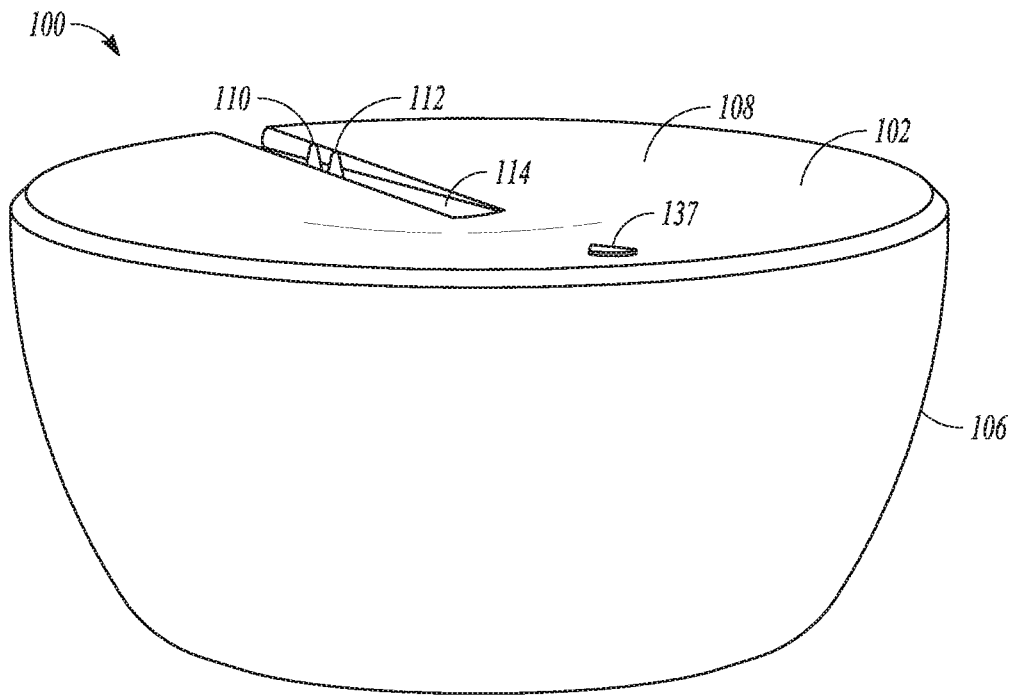
FIG. 2A is a side perspective view of an example water detection device.

FIG. 2A is a side perspective view of the example water detection device 100.

Figure 2B:
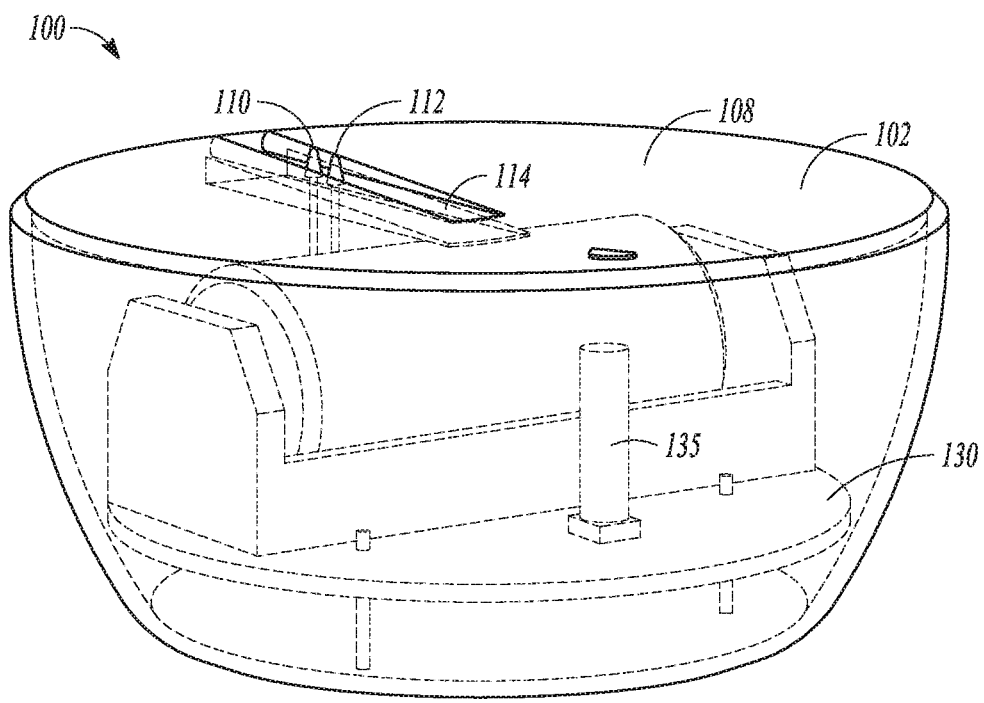
FIG. 2B is a cut-away view of the example water detection device shown in FIG. 2A.

FIG. 2B is a cut-away view of the example water detection device 100 that shows internal components. A side view of the water detection device 100 is provided in FIG. 3A, and a cut-away side view of the water detection device is provided in FIG. 3B.

The water detection device 100 may include a top surface 102, a bottom surface 104, and one or more side walls 106 extending between the top surface 102 and the bottom surface 104. The top surface may include a concave portion 108 that may be configured to collect water. Electrical contacts 110, 112, may be positioned on the top surface 102 and configured to detect the presence of water on the top surface 102. The top surface may also optionally include a channel 114 that may be configured to direct water toward the electrical contacts 110, 112. In some examples, the electrical contacts 110, 112 may be positioned in the channel 114. The electrical contacts 110, 112 may, for example, be molded into the top surface. The electrical contacts 110, 112 may also be adhered to the top surface 102, or inserted through the top surface 102. In an example configuration, the electrical contacts are spaced at a distance of 3.7 to 4.3 millimeters (mm) from each other. In an example, the contacts are spaced about 4 millimeters apart. While two electrical contacts are shown in the illustrated example, the water detection device 100 may include three or more electrical contacts in the top surface 102.

Figure 3A:
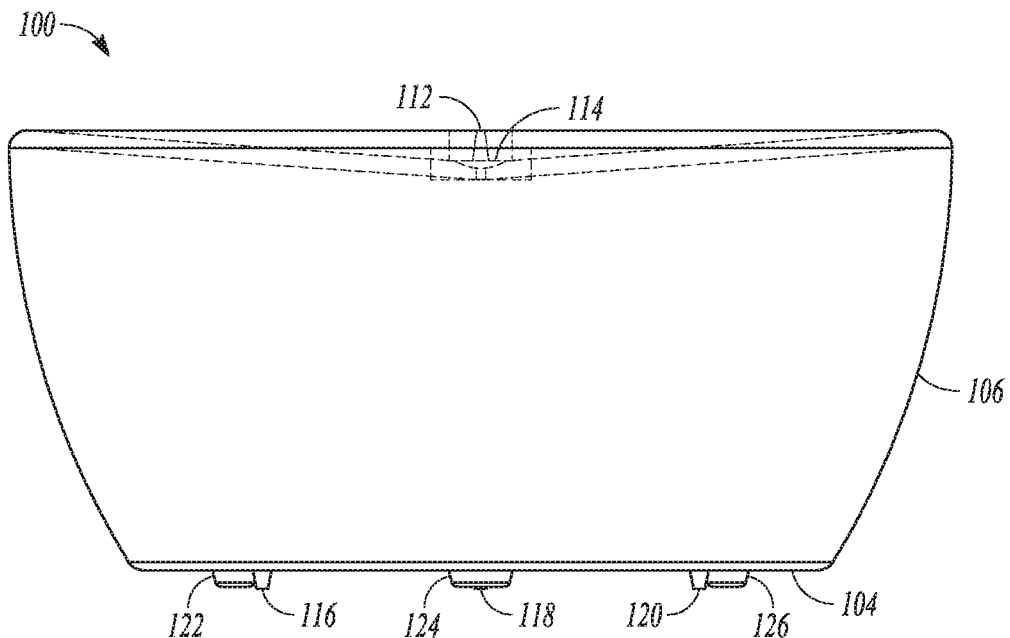
FIG. 3A is a side view of an example water detection device.
Figure 3B:
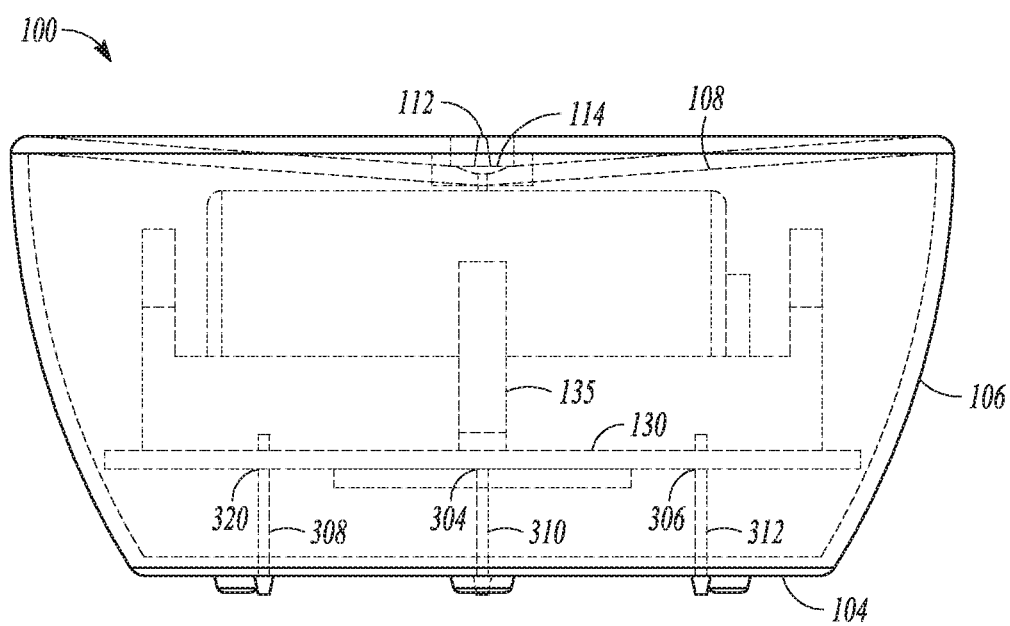
FIG. 3B is a cut-away view of the example water detection device shown in FIG. 3A.

Electrical contacts 116, 118, 120 may also be provided at the bottom surface 104 of the water detection device 100, as shown in FIGS. 3A and 3B. While three electrical contacts are shown in the bottom surface 104 of the device, other examples include just two electrodes on the bottom surface 104, or four or more electrodes. The water detection device 100 may include one or more feet 122, 124, 126 extending from the bottom surface 104. The feet 122, 124, 126 may be configured to space the electrical contacts from a floor or other resting surface, and to allow water to flow beneath the bottom surface 104 of the device. In some examples, the feet 122, 124, 126 may be configured to create a space between the bottom surface 104 and the floor of about 0.7 to 1.3 millimeters. In an example the feet 122, 124, 126 may be configured to create a space of about 1 millimeter. In some examples, the electrical contacts may protrude from the bottom surface 104 and have a bottom dimension that is approximately coplanar with the feet 122, 124, 126, i.e., so the electrical contacts "touch the floor". In other examples, the electrical contacts 116, 118, 120 may be configured to be spaced from the floor (e.g. shorter than the feet) a distance of about 1.85 to 2.15 millimeters. In an example the electrical contacts 116, 118, 120 may be space from the floor about 2 millimeters. In some examples, a bottom portion 128 of the water detection device 100 may be curved or tapered toward the bottom of the device 100, which may direct water to the space below the device 100.

The electrical contacts 110, 112, 116, 118, 120 may be operatively coupled to a circuit board 130 (shown in FIGS. 2B and 3B) that may be housed inside of the water detection device 100. The circuit board 130 may include circuitry that may be configured to deliver a pulse to one or more electrical contacts and, when water is present to complete an electrical circuit, sense the pulse at one or more other contacts. The water detection device 100 may also include a battery compartment 132 and a battery 133 situated in the battery compartment. The water detection device 100 may also include one or more light emitting diodes 135, which may be coupled to the circuit board 130 and configured to be visible through an optional window 137 in the top surface 102 of water detection device, which may be useful to a user to confirm power status (e.g., battery charge state).

Figure 4:
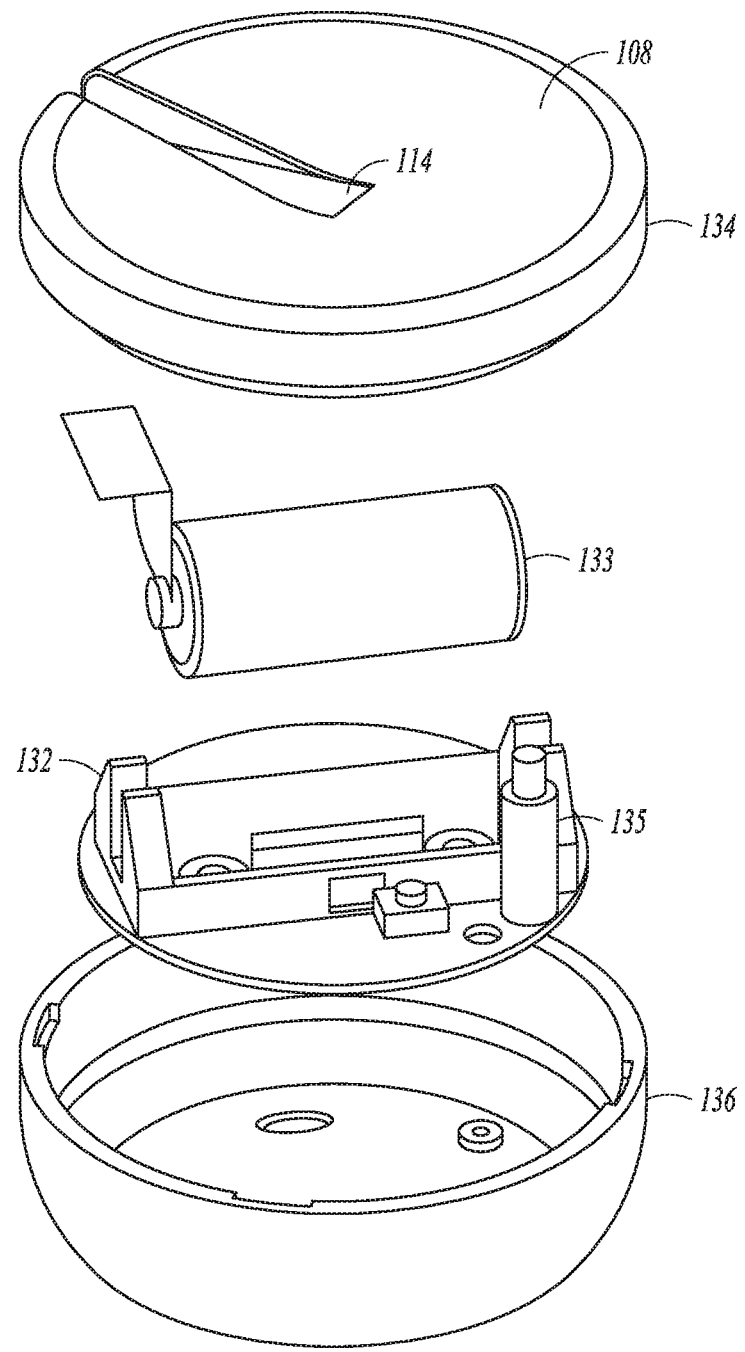
FIG. 4 is an exploded view of an example water detection device.
Figure 5:
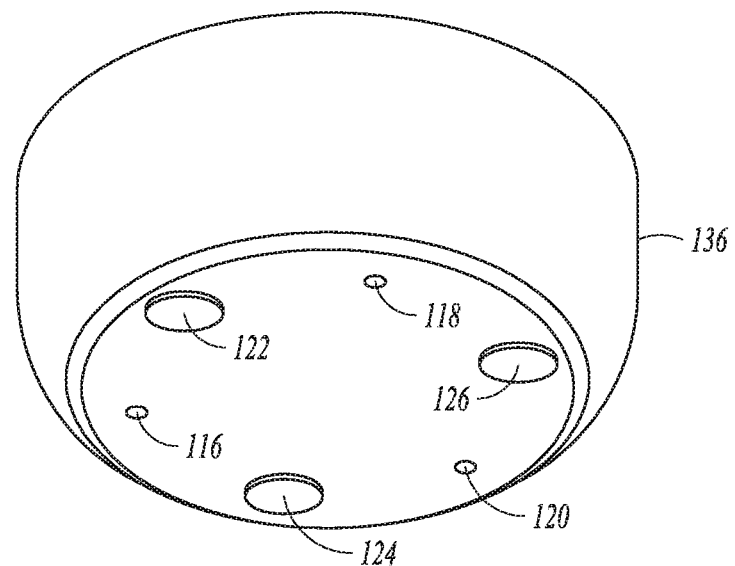
FIG. 5 is a perspective bottom view of a housing for a water detection device.
Figure 6:
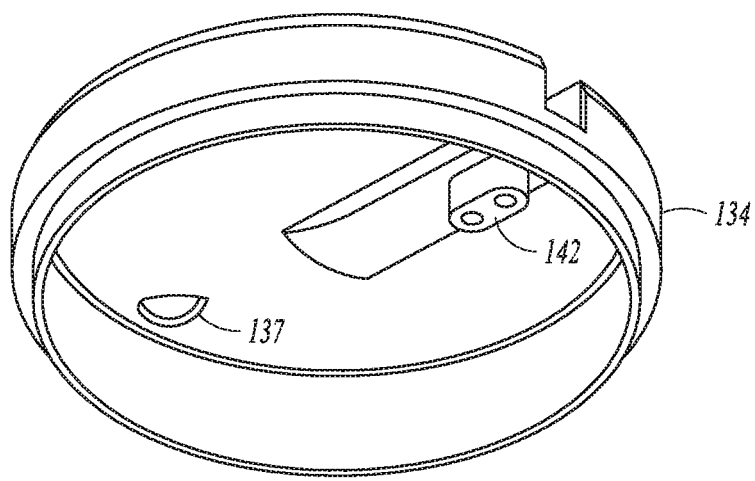
FIG. 6 is a bottom perspective view of a cover for a water detection device.

FIG. 4 is an exploded view of an example water detection device. The water detection device 100 may be configured to include a housing assembly 150 that may include a top portion (e.g., cover) 134 configured to couple with a bottom portion 136 of the housing assembly 150. FIG. 5 is a perspective bottom view of the bottom portion 136 of the housing. FIG. 6 is a bottom perspective view of the top portion (cover) 134. The top portion cover 134 may include the concave portion 108 of the top surface 102 and the optional channel 114. As shown in FIG. 6, the channel 114 may extend to an edge 138 of the top surface 102 (i.e., to the edge 138 of the top portion (cover) 134 in FIG. 6), which may allow water to flow off the top cover and, depending on the shape of the surface (floor) below the water detection device 100, eventually pool around the electrical contacts 116, 118, 120. A protrusion 140 may be formed on a bottom side 142 of the top portion 134 of the housing assembly 150. The protrusion 142 may be configured to receive mechanically-biased electrical contacts (discussed below). For example, electrical contacts may be assembled into the top surface and the protrusion, or molded (e.g., insert molded or over molded) into the top portion 134.

Figure 7:
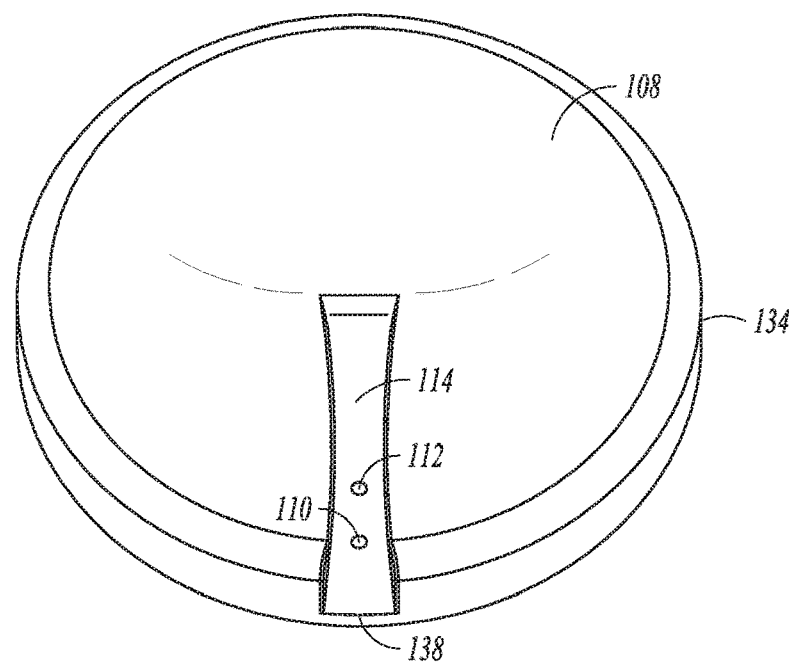
FIG. 7 is a top perspective view of the cover for a water detection device shown in FIG. 6.

FIG. 7 is a top perspective view of the cover for a water detection device 100.

Electrical contacts 110, 112 are shown placed in channel 114.

Figure 8:
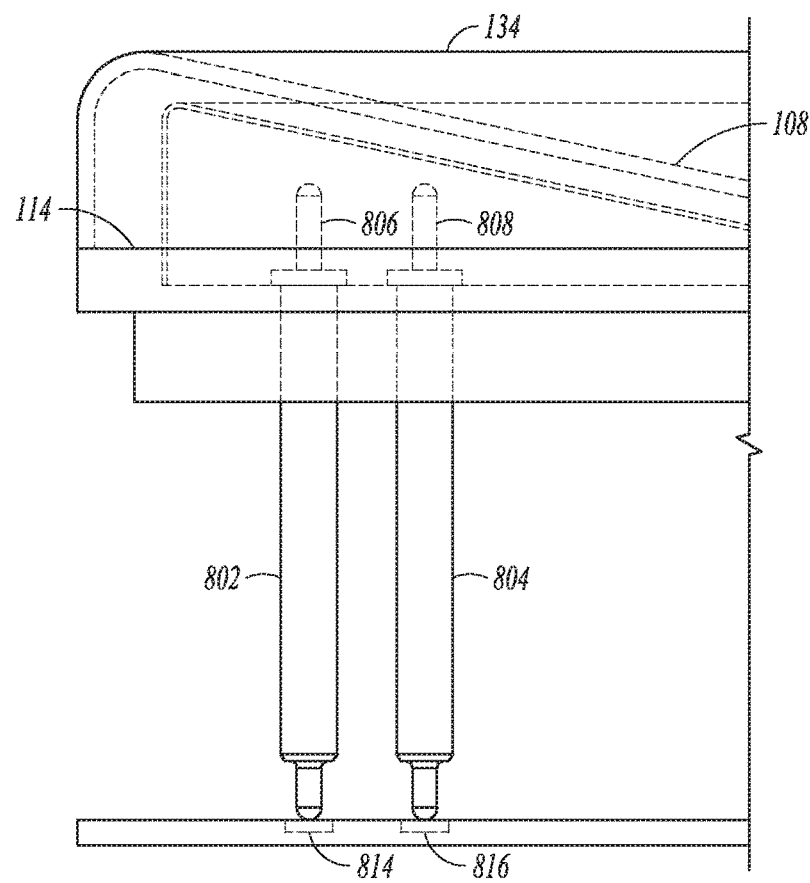
FIG. 8 is a side view of a portion of a water detection device showing mechanically biased electrical connectors.

FIG. 8 is a side view of a portion of a water detection device showing mechanically biased electrical connectors 802, 804 coupled to the top portion 134 of the water detection device 100.

Top ends 806, 808 of the electrical connectors 802, 804 may extend to the top surface 102 of the device 100. In some examples, top ends 806, 808 of the electrical connectors couple directly or indirectly to the electrical contacts 110, 112.

In other examples, the top ends form the electrical contacts 110, 112. In varying examples, the top ends 806, 808, may protrude through the top surface 102, or may be flush with the top surface, or may be recessed in holes in the top surface. The bottom ends 810, 812 of the electrical connectors 802, 804 may be configured to electrically connect with contact pads 814, 816 (shown in FIG. 9), which may be positioned on a printed circuit board 900 (also shown in FIG. 9). In some examples, the electrical connectors 802, 804 may be mechanically biased to provide electrical contact with the circuit board. For example, the electrical connectors 802, 804 may include one or more springs that bias the top ends 806, 808 or the bottom ends 810, 812 or both against the contact pads 814, 816. In some examples, the connectors, mechanically-biased electrical connectors may be spring-loaded. For example, a spring (not shown) may be assembled into electrical conductor housings 818, 820. In other examples, the bottom portions or top portions may include springs, or may be springs (e.g., leaf springs). In some examples, the electrical connectors 802, 804 may be pogo pins.

Figure 9:
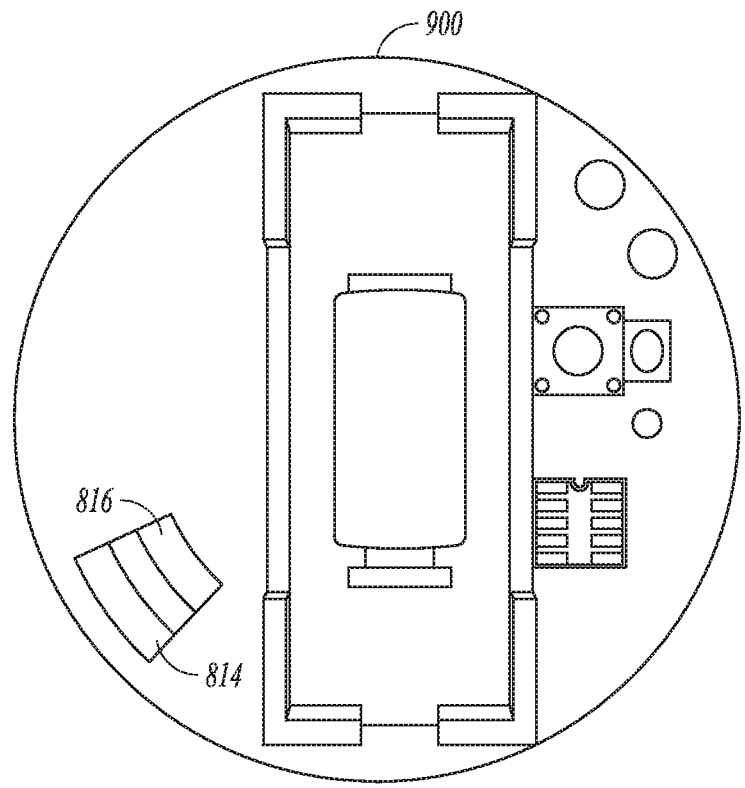
FIG. 9 is a top view of an example circuit board for a water detection device.

FIG. 9 is a top view of an example circuit board 900 configured to be assembled into the bottom portion 136 of the device. The circuit board 130 in FIG. 3A may be configured as the circuit board 900 shown in FIG. 9.

In an example configuration, the top portion 134 of the device may be configure to rotationally assemble (e.g., twist) onto the bottom portion 136. To accommodate rotational contact or rotational dimensional tolerances, the contact pads 814, 816 on the circuit board 900 may be formed in an arc.

In addition to the contact pads 814, 816 on the top side 902 of the circuit board 900, the circuit board 900 may also include contact pads 302, 304, 306 (shown in FIG. 3B) configured to electrically connect with connectors 308, 310, 312 (shown in FIG. 3B) that connect with electrical contacts 116, 118, 120 (shown, e.g., in FIG. 5) on the bottom of the water detection device 100.

Figure 10:
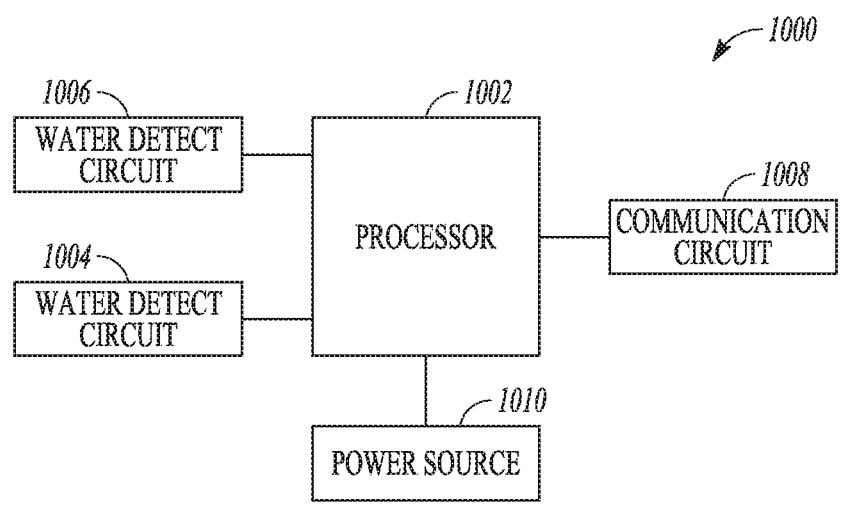
FIG. 10 is a block diagram that shows components of an example water detection device.

FIG. 10 is a block diagram 1000 that shows high-level components of an example water detection device. A processor 1002 may be coupled to a first water detection circuit 1004, that may for example be coupled to electrical contacts 110, 112 on a top side of the water detection device 100. The processor 1002 may also be coupled to a second water detection circuit 1006, that may for example be coupled to electrical contacts 116, 118, 120 on a bottom side of the water detection device 100. The water detection circuits may be configured to notify the processor when water is detected (for example, using methods and circuits described below). The processor may trigger an alert and communicate the alert via a communication circuit 1008, which may, for example, include a wireless communication circuit, transceiver, and antenna. The communication circuit may be configured to operate using a standard protocol such as Bluetooth, Zigbee, Z-Wave, WiFi or other communication methods. A water detection alert may be sent to a hub, cellular phone, or other device. The alert may be delivered to a user via an electronic device, such as a mobile device. The processor may be coupled to a power source 1010, such as battery, and may distribute power to the water detection circuits 1004, 1006 and the communication circuit 1008. In another configuration, the power source 1010 may be directly coupled to the water detection circuits or communication circuit through a bus or other electrical connection.

Figure 11A:
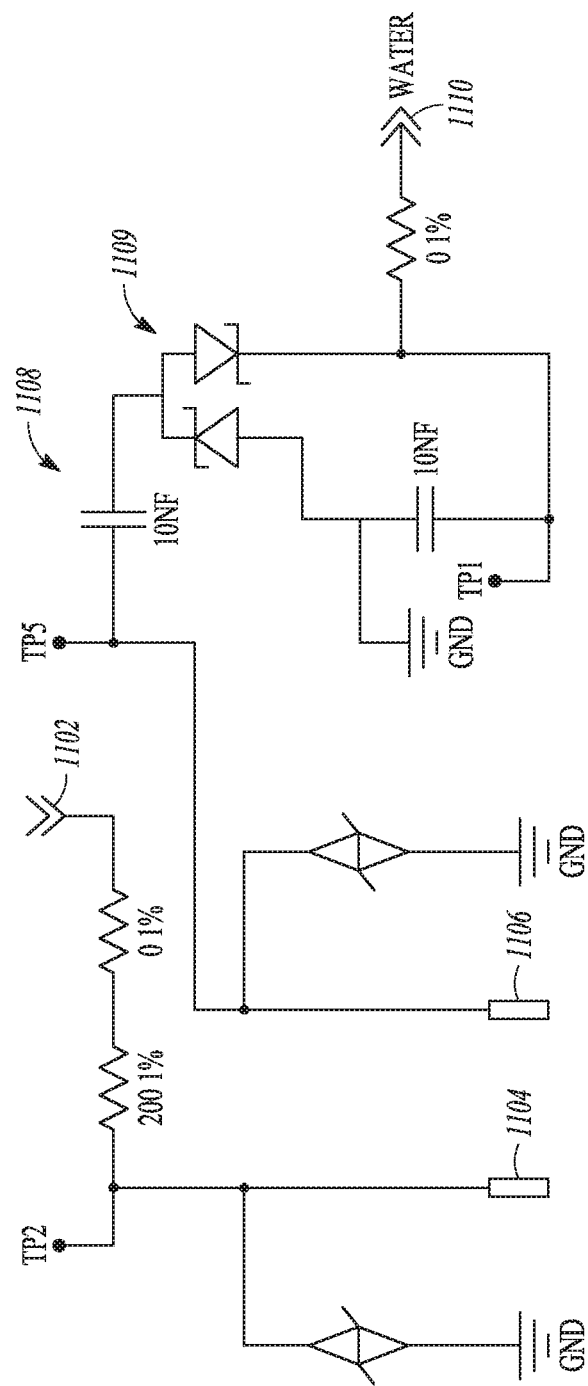
FIGS. 11A and 11B are illustrations of an example water detection.

FIG. 11A is a schematic illustration of an example water detection circuit 1100. A water detection signal may be injected at an input 1102 to an electrical contact 1104. In the presence of water, the injected signal may be conducted through the water and received at a second (receiving) electrical contact 1106. The received signal may be passed through a filter 1108 and diode 1109 to an output 1110. The electrical contacts 1104, 1106 may be the electrical contacts 110, 112. In an example, a third electrical contact (not shown) may be provided in the circuit, in which case the signal may be delivered through one contact and sensed by the other two circuit, or may be delivered through two contacts and sensed by one electrical contact. As will be described in further detail below, the signal may be delivered as an oscillating signal. In some examples, switching circuitry may be used to deliver control delivery of the circuit, e.g., to delivering recurrent (e.g., intermittent) pulses to save energy, or to switch which contact(s) are delivering the signal and which contact(s) are receiving the signal.

Figure 11B:
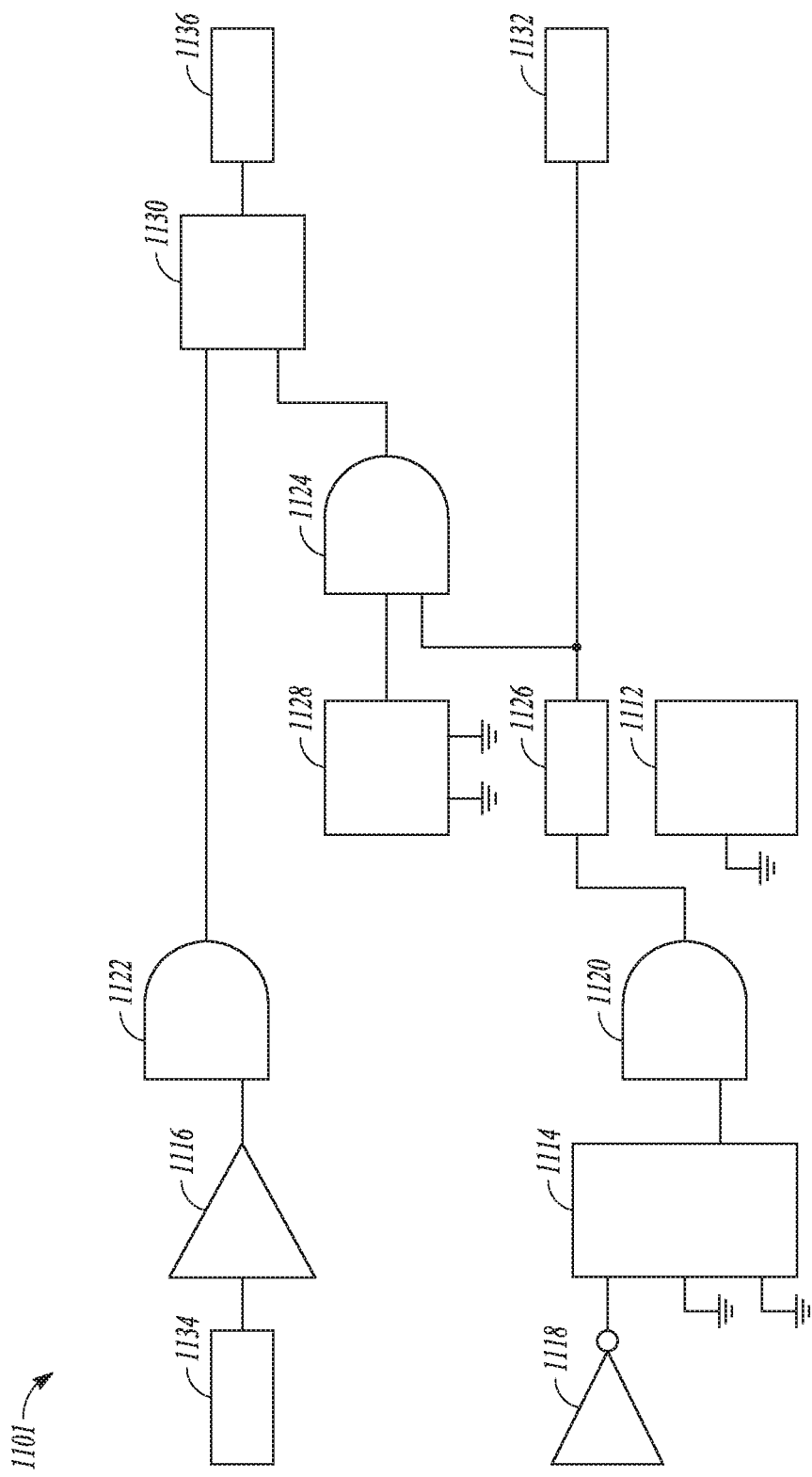

FIG. 11B is a schematic illustration of an example water detection circuit 1101 that may increase water sensitivity or specificity or both, and may conserve battery power. For example, the water detection circuit may increase sensitivity using a comparator with hysteresis (e.g., to avoid chatter when a detection signal is hovering near a threshold), or a debouncing circuit to increase accuracy or specificity of detection (e.g., only triggering a water alert when a water detection signal is registered a specified number of times (e.g., fifty (50) sequential position water detection readings), or a wake-sleep circuit configured to conserve power by shutting down functions during sleep times.

An example water detection circuit 1101 may include a wake-sleep controller circuit 1112, an oscillator circuit 1114, comparator circuit 1116, an inverter circuit 1118, a first gate 1120, second gate 1122, third gate 1124, first delay 1126, second delay 1128, a clocked latch (e.g., flip-flop) 1130, a first electrical contact 1132, a second electrical contact 1134, and water alert output 1136. The first gate 1120, second gate 1122, third gate 1124 may be logical gates configured to execute an operation, such as an AND operation.

Figure 12:
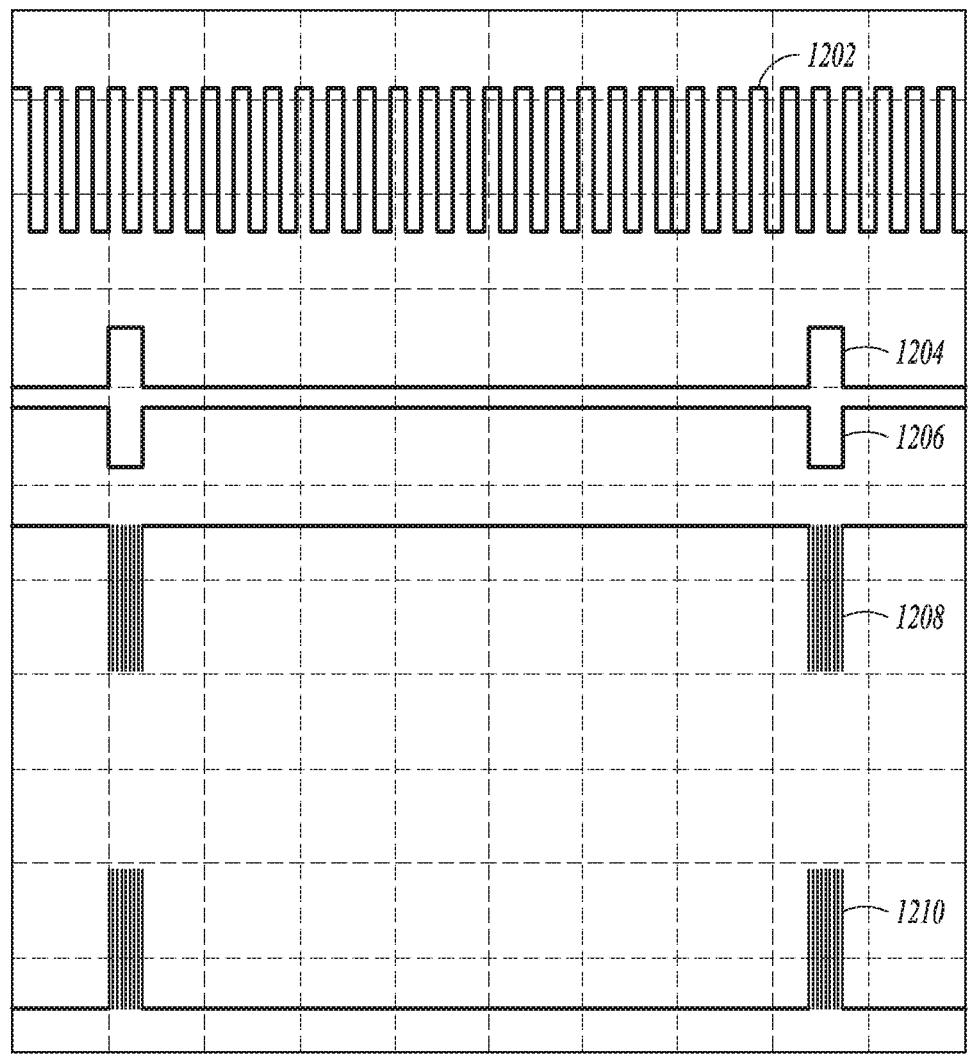
FIG. 12 is an illustration of outputs from components of an example water detector circuit.

FIG. 12 is an illustration 1200 of outputs from components of the example water detection circuit 1101 shown in FIG. 11B. The oscillator circuit 1114 may generate a first output 1202, which may for example be 109 Hz. The wake-sleep controller circuit 1112 may receive the first output 1202, measure a cycle of 185 milliseconds (ms), and generate a wake-sleep signal 1204 that includes a wake-up pulse of about 11 milliseconds (ms) and a sleep signal (e.g., 0V) for the rest of the 185-millisecond cycle. The wake-sleep signal 1204 may passed through the inverter circuit 1118 to produce an inverted signal 1206, which may be fed back into the oscillator circuit 1114 as an active high power down signal for the 25 kHz oscillator (e.g., to conserve energy). The oscillator circuit 1114 may generate a high-frequency (e.g., 25 kHz) output 1208, which may be provided as input to the first gate 1120. The first gate 1120 may combine (e.g., perform an AND operation) the high-frequency gated output 1208 and the wake-sleep signal 1204 to produce a water detect signal 1210. While the illustrated circuit shows an oscillator circuit 1114 that provides both the low (e.g., 109 Hz) and high (e.g., 25 kHz) frequency signals, these signal may also be provided by separate circuits. In some examples, the oscillator circuit 1114 and first gate 1120 may form a signal generator circuit. In some examples, a wake-sleep circuit, oscillator circuit 1114, and first gate 1120 together may form a signal generator circuit.

In the presence of liquid water, the water detect signal 1210 may be detected at the second electrical contact 1134. The detection at the second electrical contact 1134 may be used to trigger a water alert. The high-frequency oscillation may help avoid corrosion at the electrical contacts 1132, 1134 or elsewhere in the circuit. The pulsed signal (gated by the wake-sleep signal 1204) may conserve battery power while providing near-continuous monitoring.

Figure 13A:
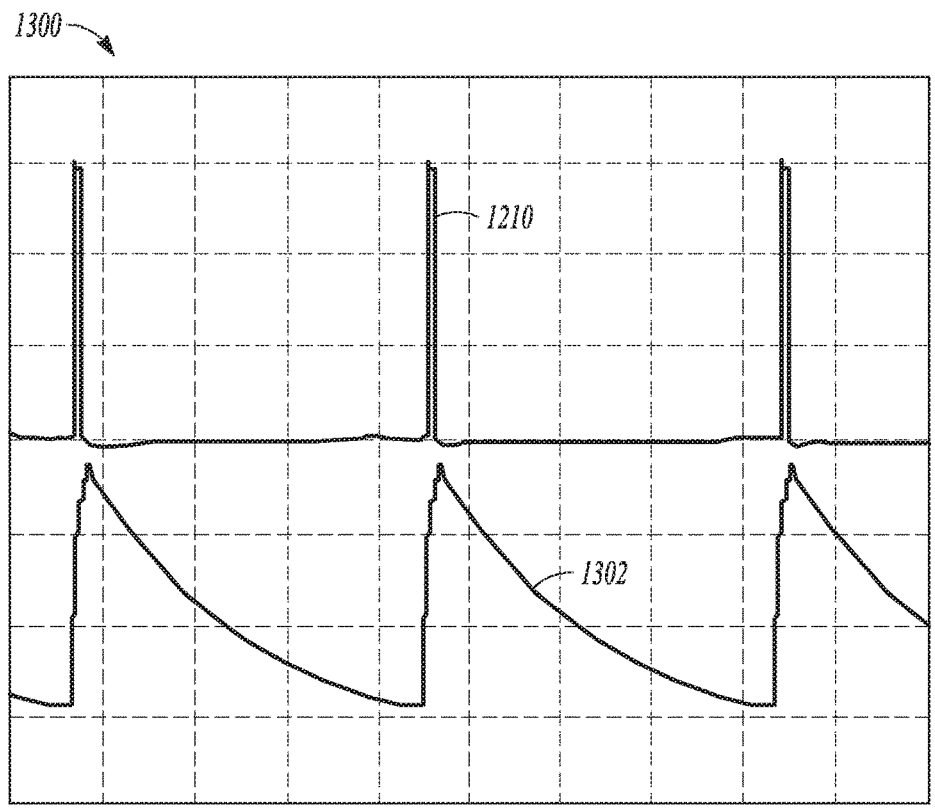
FIG. 13A is an illustration of an example output from a first contact and a signal detected at a second electrical contact.
Figure 13B:
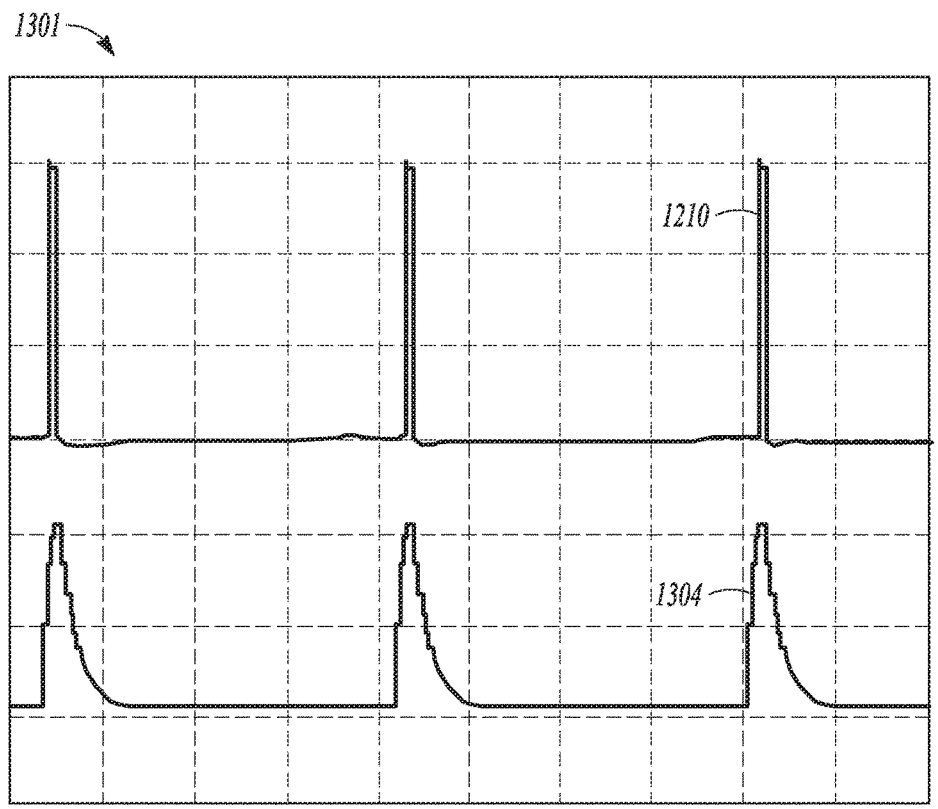
FIG. 13B is an illustration of the output from the first contact of FIG. 13A, and the signal at the second electrical contact passed through a comparator with hysteresis.

The water detection circuit 1101 may perform additional signal processing to improve the performance of the water detector circuit. FIG. 13A is an illustration 1300 of the water detect signal 1210 delivered through the first electrical contact 1132 and a raw signal 1302 detected at the second electrical contact 1134. The time scale of the illustrations 1300, 1301 of FIGS. 13A and 13B is double the scale of FIG. 12 (e.g. FIG. 12 may show 250 ms, and FIGS. 13A and 13B may show 500 ms). The water signal may be highly attenuated due to the relatively low conductivity of detected water. The raw signal 1302 may be delivered to a comparator with hysteresis 1116 and second gate 1122 to produce signal 1304 (shown in FIG. 13B), which may be delivered to the second gate 1122. The second gate 1122 may generate a second gate 1122 output (not shown) that may, for example, indicate whether the water detect signal 1210 has been detected. FIG. 13B is an illustration of the water detect signal 1210 and the output of the comparator with hysteresis 1116. A comparison of the raw signal 1302 shown in FIG. 13B with the output signal 1304 of the comparator with hysteresis 1116 in FIG. 13B shows that the signal is strengthened by the comparator circuit 1116, which may make the signal more easily or reliably detectable. For example, the hysteresis provided by the comparator circuit 1116 may prevent the second gate 1122 from chattering when the second gate 1122 is close to its threshold, which may increase the sensitivity of the water detect circuit.

Figure 14:
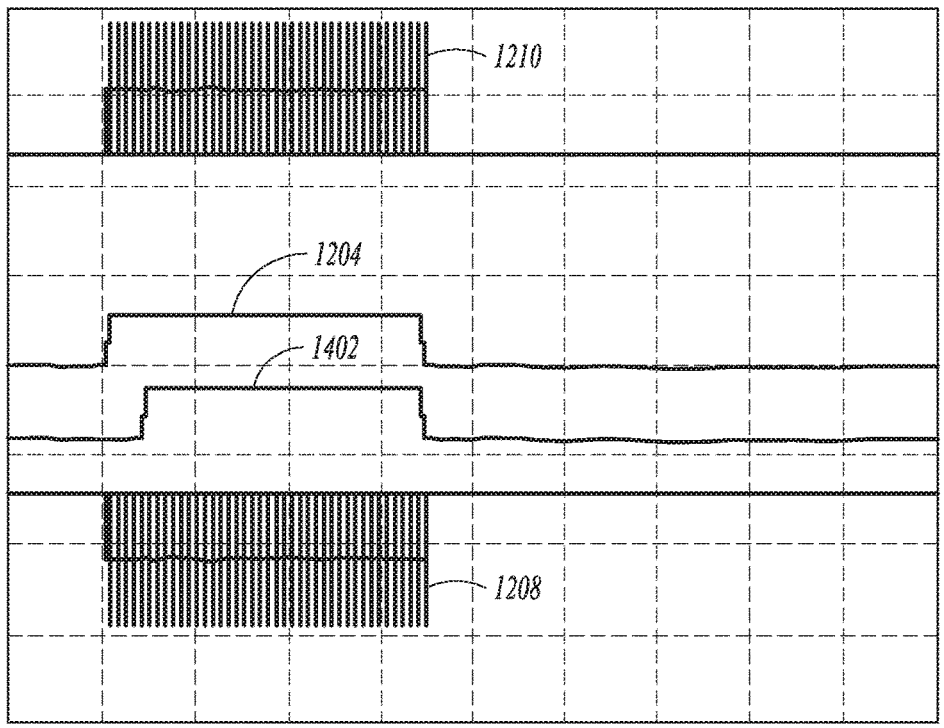
FIG. 14 is an illustration of example outputs of various components of the water detector circuit shown in FIG. 12.
Figure 15:
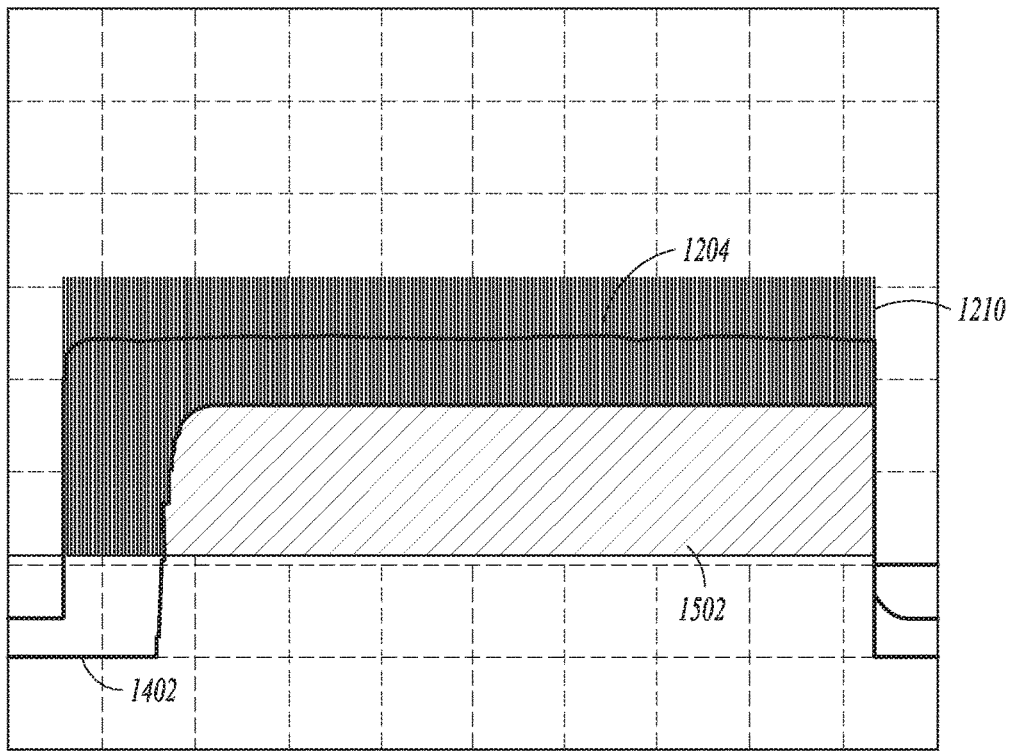
FIG. 15 is an illustration of the output of an example comparator that adds

FIG. 14 is an illustration 1400 of example outputs of various components of the water detector circuit shown in FIG. 12. The time scale of FIG. 14 is 1/10 the time scale of FIG. 12 (e.g. FIG. 12 may show 250 ms, and FIG. 14 may show 25 ms). FIG. 14 shows the water detect signal 1210 (not drawn to scale in FIG. 14), the wake-sleep signal 1204, and a delay 1402 generated by first delay 1126. The third gate 1124 may combine (e.g., perform an AND operation on) the water detect signal 1210, the wake-sleep signal 1204, and the delay signal (e.g., shown as 1 ms delay) of the wake-sleep signal generated by first delay 1126 to produce a gate output 1502 (shown in the illustration 1500 of FIG. 15) that may be provided as an input to the latch circuit 1130.

The latch circuit 1130 (e.g., flip-flop) may receive the output of the second gate 1122 as input. The latch circuit 1130 be clocked by the gate output 1502. The latch circuit 1130 may be configured as a debouncing circuit. For example, the latch may be configured to county positive water detection signals from second gate 1122 and trigger a water alert when a water alert condition is satisfied. For example, the latch circuit 1130 may trigger a water alert when a specified number (e.g., 50) of sequential water detection signals are received.

In some examples, first electrical contact 1132 or second electrical contact 1134 (or both) may include two or more electrically connected contacts, which may increase the likelihood of detection of water near the sensor (e.g. if water is present only at certain locations on or below the sensor.) In some example, a water detection circuit may include three or more electrical contacts that may be gated or switched to allow for water sensing via different contacts, or different combinations of contacts, which may, for example, increase sensitivity to the presence of water, or may increase durability because of redundancy of electrical contacts (e.g., if a contact became corroded, damaged, or electrically shorted.

In some examples, water detection device may include two or more circuits.

A water alert may be delivered to another device or circuit, such as a processor or master controller, and eventually through a network to a user.

Each of these non-limiting examples may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A water detection device comprising:
   a housing including a removable cover;
   a first water sensor coupled to a top of the housing;
   a second water sensor coupled to the bottom of the housing;
   a circuit board and a mechanically biased electrical contact coupled to the removable cover; and
   a water detection circuit including:
      an oscillator circuit coupled to the first electrical contact and configured to deliver an oscillating pulse to the first electrical contact;
      an analog comparator circuit with hysteresis, the analog, comparator circuit coupled to the second electrical contact; and
      a water alert circuit coupled to the analog comparator circuit, the water alert circuit configured to declare a water event alert responsive to detection of the oscillating pulse at the second electrical contact, wherein:
      the mechanically biased electrical contact electrically couples the first water sensor to the circuit board, the mechanically biased electrical contact is configured to apply force against a mating receptacle,
      the first water sensor includes a first electrical contact and a second electrical contact;
      the water detection circuit is configured to deliver a water sensing pulse to the first electrical contact, and
      the water sensing pulse is detectable by the water detection circuit through the second electrical contact in the presence of water between the first electrical contact and second electrical contact.

2. The water detection device of claim 1, wherein the housing has a concave top surface configured to direct water centrally upon the top surface.

3. The water detection device of claim 2, wherein the housing has a canal in the concave top surface configured to direct water toward the first water sensor.

4. The water detection device of claim 1, wherein the mechanically biased electrical contact includes a pogo pin.

5. The water detection device of claim 1, further comprising a wireless transceiver, wherein the water detection device is configured to send an alert signal via the wireless transceiver responsive to detection of water by at least one of the first water sensor or the second water sensor.

6. The water detection device of claim 1, further comprising a direct current power source, and wherein the water detection device includes a signal modulator circuit that is coupled to the direct current power source and is configured to deliver the water sensing pulse as a pulse of alternating current to the first electrical contact.

7. The water detection device of claim 1, wherein the water detection circuit is configured to recurrently or intermittently deliver the water sensing pulse at a sampling interval.

8. A method of detecting water comprising:
   delivering an alternating current water sensing pulse to a first electrical contact;
   detecting the water sensing pulse as an attenuated signal at a second electrical contact;
   passing the attenuated signal through a low pass filter;
   applying the filtered signal as an input to a gate;
   applying an output of the gate as an input to a latch; and
   declaring a water event responsive to the input to the latch meeting a water event condition.

9. The method of claim 8, wherein the water event condition includes a specified number of positive water signal sequential inputs.

10. The method of claim 9, comprising delivering the alternating current water sensing pulse according to a sampling interval.

* * * * *